(12) United States Patent
Chinnappan et al.

(10) Patent No.: US 10,788,488 B1
(45) Date of Patent: Sep. 29, 2020

(54) FULL-LENGTH AND TRUNCATED ANTI-COAGULANT DABIGATRAN ETEXILATE SPECIFIC DNA APTAMERS FOR ELECTROCHEMICAL AND FLUORESCENCE SENSING APPLICATIONS

(71) Applicant: Alfaisal University, Riyadh (SA)

(72) Inventors: Raja Chinnappan, Riyadh (SA); Mohammed Zourob, Riyadh (SA); Shimaa Eissa, Riyadh (SA); Maher M Aljohani, Riyadh (SA)

(73) Assignee: Alfaisal University, Riyadh (SA)

( * ) Notice: Subject to any disclaimer, the term of this patent is extended or adjusted under 35 U.S.C. 154(b) by 0 days.

(21) Appl. No.: 16/680,685

(22) Filed: Nov. 12, 2019

(51) Int. Cl.
*A61K 48/00* (2006.01)
*C07H 21/04* (2006.01)
*G01N 33/553* (2006.01)
*G01N 33/53* (2006.01)
*C12N 15/115* (2010.01)

(52) U.S. Cl.
CPC ......... *G01N 33/553* (2013.01); *C12N 15/115* (2013.01); *G01N 33/5308* (2013.01)

(58) Field of Classification Search
CPC ............................... A61K 45/06; C12N 15/113
See application file for complete search history.

(56) References Cited

U.S. PATENT DOCUMENTS 8,388,907 B2 * 3/2013 Gold ..................... B01L 3/5029
422/406
2016/0131668 A1 * 5/2016 Roncancio ........... G01N 33/946
436/501
2018/0067108 A1 * 3/2018 Blust .................. G01N 33/5308
2018/0305695 A1 * 10/2018 Hirao ................. A61K 31/7115

FOREIGN PATENT DOCUMENTS

EP 2980218 A1 * 3/2016 ........... C12N 15/113

OTHER PUBLICATIONS

Aljohani et al. (Sci Rep, Sep. 5, 2018, 8(1), pp. 1-8).*

* cited by examiner

*Primary Examiner* — Amy H Bowman
(74) *Attorney, Agent, or Firm* — Geeta Kadambi; Riddhi IP LLC

(57) ABSTRACT

The developed long and short aptamer sequences can be used as high affinity and specificity tools to analyze the drug Dabigatran etexilate for therapeutic drug monitoring, pharmacokinetic and naturalization studies. Using the technique by performing several rounds of selection and enrichment with a randomized 60-mer DNA library, a number of specific aptamer sequences were successfully selected for Dabigatran etexilate. We evaluated the binding affinity and specificity of the generated aptamers showing dissociation constants ($k_d$) ranging from 47-312 nM and very weak or no cross-reactivity to other analytes. Complimentary sequences labelled with a fluorophore and a quencher was used for mapping the binding region within the aptamer by monitoring the change in the fluorescence signal. A truncated sequence was used to construct a turn-on fluorescence sensor. The application of the long and short sequences in electrochemical and fluorescence sensors, respectively implying the usefulness of these aptamers in Dabigatran etexilate diagnostics applications and has unique potential of clinical uses in the near future.

10 Claims, 8 Drawing Sheets
Specification includes a Sequence Listing.

FULL-LENGTH AND TRUNCATED ANTI-COAGULANT DABIGATRAN ETEXILATE SPECIFIC DNA APTAMERS FOR ELECTROCHEMICAL AND FLUORESCENCE SENSING APPLICATIONS

FIELD OF TECHNOLOGY

A method to detect the anticoagulants drug—Dabigatran etexilate using either full length or truncated single-stranded oligonucleotides is disclosed. The sequence file RIPLLC032014US1_ST25 created on Nov. 12, 2019 with a 8 kb size is being submitted.

BACKGROUND

Dabigatran etexilate is a new direct oral anticoagulants (DOACs) acting by direct inhibition of thrombin. This drug increasingly used for number of blood thrombosis conditions. It is approved by The Food and Drug Administration (FDA) for reducing the risk of strokes and systemic emboli among patients with atrial fibrillation (AF). Dabigatran etexilate is the active form of the commercially available prodrug Dabigatran etexilate (PRADAXA).

Although Dabigatran etexilate has many superior advantages over the standard oral anticoagulant drug warfarin, lack of specific laboratory tests is the most important obstacle of using this new anticoagulant. Continuous monitoring is required in patients with renal failure, injury, drug overdose, over/underweight patients or in conditions of urgent need for surgical interventions or excessive bleeding. There is an urgent need to create a sensitive and quick test so lives can be saved and effective use of this drug can be made.

SUMMARY

In this work, a novel long and short aptamers for Dabigatran etexilate were selected for uses in diagnostics and therapeutics studies. In one embodiment, a Systematic evolution of ligands by exponential enrichment (SELEX) to generate single-stranded oligonucleotides against the anticoagulants drug—Dabigatran etexilate was done. In another embodiment, a 60-mer aptamer was then integrated in electrochemical sensing platform for Dabigatran etexilate detection. Then, Complimentary sequences labelled with a fluorophore and a quencher was used for testing the binding region within the aptamer by monitoring the change in the fluorescence signal. The 60-mer aptamer was truncated to multiple shorter copies including a 38 nucleotides sequence. The truncated 38-mer sequence was used to construct a turn-on fluorescence sensor.

Following several rounds of selection and enrichment with a randomized 60-mer DNA library, a number of specific aptamer sequences were successfully selected for Dabigatran etexilate. We evaluated the binding affinity and specificity of the generated aptamers showing dissociation constants ($k_d$) ranging from 47-312 nM and very weak or no cross-reactivity to other analytes. Application of one of the selected aptamers in an electrochemical biosensor was successfully performed and showed high sensitivity and selectivity. This aptamer was then truncated to a 38-mer sequence showing 47 fold high affinity compared to the original aptamer. A Turn-on fluorescence sensor was then developed using the short aptamer showing a detection limit of 1 nM. The performance of the fluorescence sensor was examined in blood serum samples and showed excellent recovery percentages exceeding 98%. In one embodiment, this method can be used for any drug.

Other features will be apparent from the accompanying drawings and from the detailed description that follows.

BRIEF DESCRIPTION OF DRAWINGS

Example embodiments are illustrated by way of example and not limitation in the figures of the accompanying drawings, in which like references indicate similar elements and in which.

Figure 1:
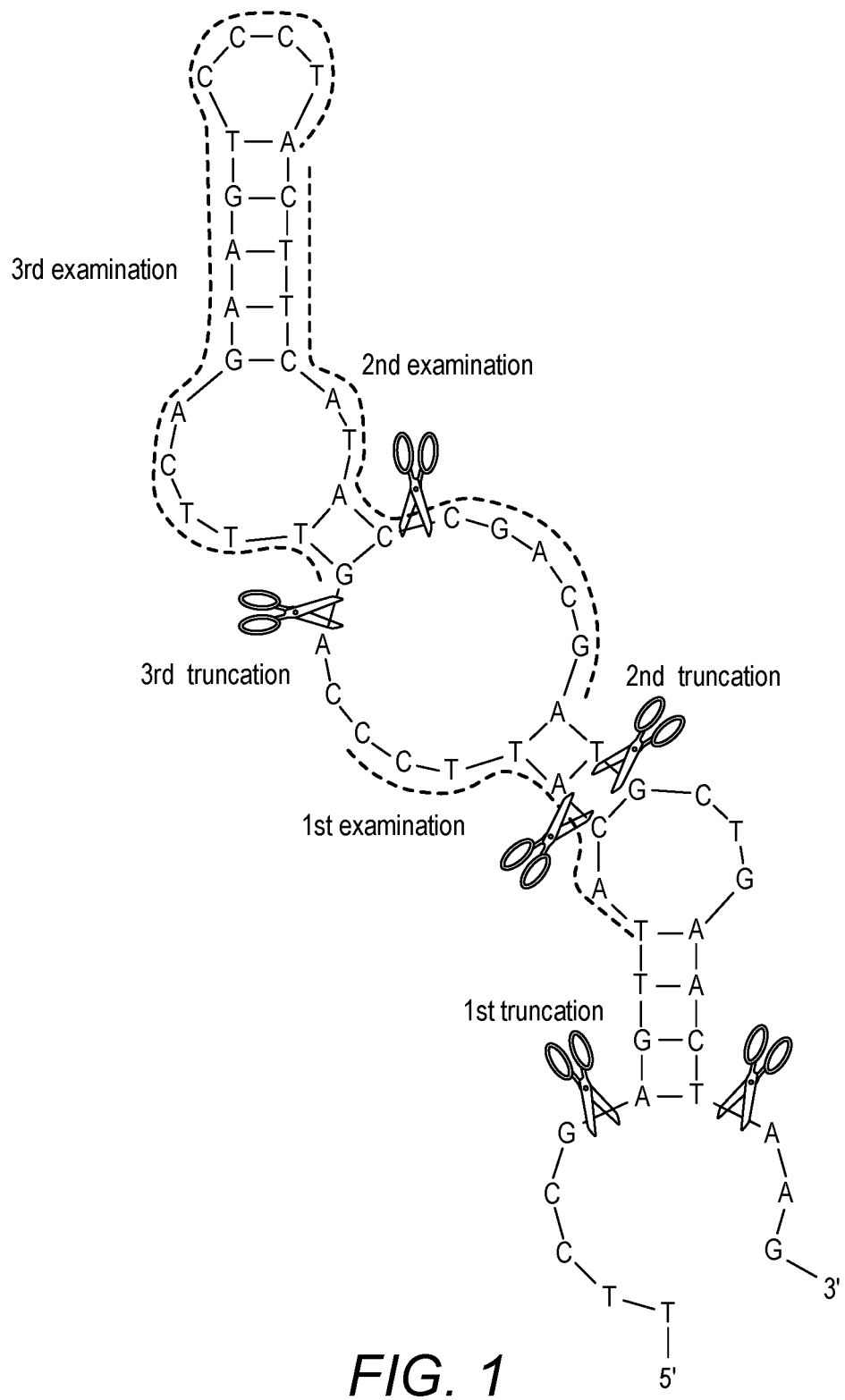
FIG. 1 shows mfold predicted secondary structure of the 60-mer (Dabigatran) DBG aptamer of SEQ ID NO: 1.

Other features of the present embodiments will be apparent from the accompanying drawings and from the detailed description that follows.

DETAILED DISCUSSION

Dabigatran etexilate is a new therapeutic class of anticoagulant for patients at high risk for thrombosis. In 2011, Dabigatran etexilate was approved by Food and Drug Administration (FDA) to be used to prevent or reduce the risk of strokes and systemic embolism caused by nonvalvular atrial fibrillation (AF). Dabigatran etexilate is a synthetic small molecule oral pro-drug that rapidly converts into Dabigatran etexilate, a competitive, reversible and direct thrombin inhibitor with high specificity and potency Since thrombin participates in a number of critical functions in the clotting (coagulation) cascade, including the conversion of fibrinogen to fibrin. Inhibitors of thrombin can used to control the blood coagulation process in order to prevent thromboembolism formation. There are several drugs that can use this technology to evaluate how much to dose a patient and selection method can be used for optimizing dosage, recovery and follow up treatment. Even additive drugs can be controlled using these techniques.

As the first direct oral anticoagulant (DOAC), Dabigatran etexilate represents a new era of anticoagulant agents with many preventive and curative applications. Dabigatran etexilate is gaining acceptance in clinical practice because it is not affected by food and medication interactions, and it seems to have a good safety profile. Sold under the brand name Pradaxa, Dabigatran etexilate came onto the market in 2010. This novel oral anticoagulant was first approved by FDA for use in patients with atrial fibrillation and was subsequently approved in more than 100 countries for several indications requiring anticoagulation. Dabigatran etexilate differs from the conventional anticoagulant warfarin as it interferes with thrombin, thereby providing safe and efficient anticoagulation. Since its rapid introduction, Dabigatran etexilate has continued to hold great promise. Its good safety profile, fixed-dose administration, and lack of food and drug interactions and need for frequent monitoring offer superior advantages. In addition, Dabigatran etexilate provides a broader therapeutic window than warfarin, therefore, it is being used as an alternative to warfarin for stroke and systemic embolism prevention in patients with nonvalvular atrial fibrillation (NVAF). Dabigatran etexilate is used to be given without specific laboratory tests to identify the drug levels.

Dabigatran etexilate has a short half-life of 12 to 17 hours in patients with normal renal function. Dabigatran etexilate is mainly (80-85%) eliminated in the unchanged form via glomerular filtration, thus renal function is an important determinant of therapy level. The risk of bleeding is considerably higher in patients with reduced renal function, who may have impaired drug clearance. A variety of emergency or life-threatening situations require knowledge of Dabigatran etexilate levels, such as emergency surgery, assessing Dabigatran etexilate compliance, major or minor acute bleeding and thrombosis, and examining drug interactions, particularly for tailoring Dabigatran etexilate dose in patients with renal insufficiency or for those who are obese or underweight. Determining Dabigatran etexilate levels may also be needed when the reversal of Dabigatran etexilate is medically necessary, such as before using the antibody-based reversing agent Praxbind. In these clinical situations, rapid, specific, and accurate quantitative tests are needed to measure the quantity of Dabigatran etexilate in blood plasma. Conventional clinical coagulation tests (prothrombin time (PT), activated partial thromboplastin time (aPTT), and international normalized ratio (INR) measurement) are not sensitive or accurate enough to assess Dabigatran etexilate levels, a factor that can be a disadvantage in emergency situations, such as unexpected bleeding during Dabigatran etexilate therapy and before undergoing emergency surgery.

Currently, no FDA-approved method exists for measuring Dabigatran etexilate levels. The unavailability of reliable testing for Dabigatran etexilate levels makes many clinicians hesitant to prescribe Dabigatran etexilate and other DOACs because of concerns about bleeding and reversibility. Liquid chromatography-tandem mass spectrometry (LC-MS/MS) can be used to accurately determine Dabigatran etexilate levels in human plasma over a broad concentration range, but this technology exists in only a few highly specialized laboratories. It requires intensive sample preparation and working protocols that involve slow turnaround times, and it is not available 24 hours a day. Although LC-MS/MS is useful as a reference method for laboratory proficiency testing and is the gold standard for validating measurement methods for determining Dabigatran etexilate levels over a broad concentration range, it is inefficient for rapid testing in clinical laboratories or emergency rooms, reducing its usefulness. Therefore, it is not the method of choice in emergency situations. Therefore, there is a pressing need for rapid, sensitive, and point of care detection method for Dabigatran etexilate.

Modern affinity reagents known as aptamers are synthetic single-stranded (ss) oligonucleotides that have shown tremendous benefits in diagnostic, therapeutic, and sensing applications Aptamers can be derived by an in vitro combinatorial selection process termed SELEX (Systematic Evolution of Ligands by Exponential Enrichment) that enriches the number of randomized DNA or RNA libraries ($10^{14}$-$10^{15}$ sequences) to few sequence candidates capable of binding the target with high affinity. The resulting aptamer sequence are typically 30 to 70 bases in length with three main functional regions namely, target binding bucket, the supporting region, and nonessential region including primer binding sites used during SELEX PCR amplification steps.

The identification of the binding region is highly crucial for optimum performance of the selected aptamer in many transduction schemes as well as for cost reduction in aptamer sequence synthesis for therapeutic applications. In fact, small molecular weight target binding aptamers were found to show improved affinity, specificity, and sensing performance when the non-essential nucleotides were eliminated or when engineering the binding region for improved or diminished conformational change.

In this study, we have selected high affinity aptamers against Dabigatran etexilate using SELEX. The selected 60-mer aptamer sequence (SEQ ID NO: 1) was applied in a square wave voltammetry-based sensor showing good sensitivity. We then reported a method to identify the binding region of the aptamer that binds to Dabigatran etexilate. The method relies on duplexing various sections of the randomized region with 8-mer complementary sequences labelled with a fluorophore and a quencher, as shown in Scheme 1. Upon target binding, nucleotides outside the binding region will not cause displacement of the duplexed sequences and thus are truncated. However, target binding with the functional region will lead to the displacement of the complementary sequences followed by enhancement in fluorescent signals.

By applying the proposed aptamer binding region screening method, a 38-mer truncated aptamer was generated with a binding affinity of 1 nM. A signal-on displacement sensor was constructed using the 38-mer aptamer. The sensor showed high sensitivity, selectivity against biological interfering agents, and robust operation in spiked plasma/serum samples.

Materials and Methods

Experimental: Dabigatran etexilate was purchased from (Selleck, Houston, Tex., USA; https://www.selleckchem.com/). Taq plus DNA polymerase, dntps were purchased from ACE Biotech (Riyadh, Saudi Arabia). PCR2.1-TOPO cloning vector with One Shot MAX Efficiency DH5α-T1 were obtained from Invitrogen Inc, (New York USA). 2-amino-2-(hydroxymethyl)-1,3-propanediol (Tris base), sodium azide, hydrochloric acid, potassium phosphate, sodium chloride, potassium chloride, sodium hydroxide, urea, hydrochloric acid, dimethyl sulphoxide, acrylamide and bisacrylamide, sodium phosphate, magnesium chloride ethanol, dimethyl sulphoxide (DMSO) and ethylenediaminetetraacetic acid (EDTA) were purchased form Sigma-Aldrich (Saint-Louise, Mo., USA). Ultrafiltration Amicon device was obtained from Millipore (Sigma Mass. USA). All labelled and unlabelled oligonucleotides (shown in Table 1 and table 2) were synthesized and HPLC purified by Metabion International (Planegg, Germany). N-hydroxysuccinimide (NHS) activated sapharose-4B was purchased from GE healthcare (Milwakee, Wis., USA). All other chemicals were of analytical grade. Spin-X cellulose acetate centrifuge filter tubes with were purchased from Corning life sciences (Tewksbury, Mass. USA). The standard solutions of DBG were prepared in methanol and further dilutions were prepared using binding buffer. Ultrapure water (resistivity>18.2MΩ cm at 25° C.) was used to prepare DNA stock solutions and stored at −20° C. until further use. A binding buffer solution comprised of 50 mM tris-HCL (pH 7.5), 2 mM $MgCl_2$ and 150 mM NaCl was used to dilute DNA solutions, all fluorescence and CD measurements. All the fluorescein-labelled probes were carefully protected from the light throughout the experimental procedures.

Instrumentation: Electrochemical experiments were performed using The Autolab potentiostat/galvanostat instrument (PGSTAT302N, Eco Chemie, The Netherlands). The fluorescence spectra for the fluorescein labelled complementary oligonucleotides were recorded using Nanodrop ND3300 fluorospectrometer (Thermo Scientific, Canada) and/or molecular device F5 fluoromax microtiter plate reader (Sunnyvale Calif., USA) using 96 well microtiter plates. The optimal excitation and emission wavelengths were set to 470±10 nm and 525±10 nm, respectively. All measurements for fluorescence spectra were carried out in the binding buffer (pH, 7.4) at room temperature. All experiments were performed in triplicate unless otherwise mentioned. CD spectra were measured using Jasco J-815 CD Spectropolarimeter (Easton, Md., USA) instrument over the wavelength range from 200 to 350 nm scanned at 2 nm min-1. 0.2 mL was used to fill an ultra-thin quartz cell with test solutions.

Selection of the 60-mer (full-length) aptamers for Dabigatran etexilate using SELEX: The selection of the long aptamers was performed according to a previously published protocol. Briefly, the Dabigatran etexilate molecules were attached to sepharose beads and incubated with a DNA library. The library is designed to have a 60-nucleotides random part and two fixed primer-binding sites of 18 nucleotides in both sides. After incubation, the unbound DNA is removed from the mixture by washing and the bound DNA to the Dabigatran etexilate beads were collected by elution using urea solution with heating at 90° C. The eluted DNA solution is then desalted using amicon filters and amplified by PCR. The double stranded PCR product was then purified to separate the relevant ssDNA using poly acrylamide gel electrophoresis. The DNA band which corresponds to the aptamers was then cut and the DNA was extracted using freeze-thaw cycle. This DNA pool was then used to start a new SELEX cycle. After several cycles, the DNA solution is collected and cloned using PCR2.1-TOPO cloning vector with One Shot MAX Efficiency DH5α-T1 competent cells. After growing, the colonies were collected, PCR amplified and then sequenced. Then, the obtained sequences were aligned and grouped into several groups and representative sequences from each group were subjected to further binding affinity evaluation to Dabigatran etexilate. All the sequences are shown in Table 1.

TABLE 1

The selected aptamer sequences and the equilibrium dissociation constants of different aptamers:

| Sequence Name | Sequence 5' to 3' | $K_d$ |
|---|---|---|
| SEQ ID NO: 1 | TTCCGAGTTACATTCCCAGTTTCAGAAGTCCCTACTTCATACCGACGATGCTGAACTAAG | 46.8 |
| SEQ ID NO: 2 | GGATCCAGAGTGAAGGATAAAGCCGTATATGATTATTGATCCGACCCCACCATAGTACGT | 208 |
| SEQ ID NO: 3 | GGAGGTGCTGTGACTCAGTAGCTCTGTTAGTTTGTATGGCTACATGTGTGAGGGTGATAC | 312 |
| SEQ ID NO: 4 | ACAGCCAAGAGTGCGATGTATTAATCATTAACAAAACTGCCGGTGCATGCCCTCCGACCA | 59.6 |
| SEQ ID NO: 5 | AGTGAACGGACGATCAAAGACAACATATGGTCCGAATTTTGAACAGGTCGTTGGGGATGG | |
| SEQ ID NO: 6 | CGATTAAAGCATATAATAGTAGTATCCAGGGTGATAATGATGATGCTTCGAGGCAGTAGG | |
| SEQ ID NO: 7 | GAATAACGAGGAGTGTCCGGGATAGGAAGTAATCATTCTTACACATTCGCACCATGTCA | |
| SEQ ID NO: 8 | AACCGGCCCTCCGATGATTAGCTAACTGTTTGCGGTCTAATTTAGCGTTTGTTCTGTGCG | 58.2 |
| SEQ ID NO: 9 | GAACCCTGGCGTGCCCTATATTTTTCAAATTGTGATGTCTTTAGGGCCTGATAACCGAAT | |
| SEQ ID NO: 10 | TGAATAACGAGGAGTGTCCGGGATAGGAAGTAATCATTCTTACACATTCGCACCATGTCA | |
| SEQ ID NO: 11 | AAATATCGGTAAGGGTGAGTACTGTCTAGCGCCCCATTGATGTATAGGTCCCCAGTTAGG | |
| SEQ ID NO: 12 | TGTTAAGAAGACCGGTGGAGCCGCCAATCAATAGTTCAATGCCTGAGAGTGTTACGAGGG | |
| SEQ ID NO: 13 | TCAAGTATAGTACTAACAAACAGGGGGATTGACATCAAGTGTGAATAGGTAAGTATGA | |
| SEQ ID NO: 14 | GTAATGCGCGTACCGTGCGAAGGAAGTCCTCCCGGGTCAGTGTGAGTGGTTTTGTCCTTT | |
| SEQ ID NO: 15 | CCAGTACCGATTGTTGTCTTATGTGATGTATCACGTGCGTATGGATGTAAATGCCCA | |

TABLE 1-continued

The selected aptamer sequences and the equilibrium dissociation constants of different aptamers:

| Sequence Name | Sequence 5' to 3' | $K_d$ |
|---|---|---|
| SEQ ID NO: 16 | CGATGAAAAGGAATTCTTGTAGTTATGGGCTTCATCATGTGCTAATGGAGGGTGCGTGG | |
| SEQ ID NO: 17 | TCGTATAGCTAGCCCTCAATGCAGTGACCTCGGTAAACGAAGGCTTCTACAATGTGGT | 96 |
| SEQ ID NO: 18 | GCAGATGTGGGACGACTCAACGATACACGGGGCACATGTCCTGCCCGCGATGTCAGCCG | |
| SEQ ID NO: 19 | CATCGAGAGGTAGGGTCATTAGCAGGACGAGAGCGGTCTATATTCTGGGCGGATCGCTAT | |
| SEQ ID NO: 20 | AAAGAGACATTCAGTTATAAAAGTGGTCACCGGGATATTTTGCAAAGATCGACTAAGGT | |
| SEQ ID NO: 21 | TGAGTCAGGTTGTTGGACGAAATGTAGATATGTGTCATACCGACCCGCTGTCCCGCGTTA | |
| SEQ ID NO: 22 | ACGGGGACGTTGAGCCGATCGACTAAATAACGTCACGATACCGTAGTAGGGCGGATATTT | 130.6 |
| SEQ ID NO: 23 | CGAATAGGGGAGGTGCATCACAGTATACCCTTACGAGCGCATTTAGTAGTGTTAAGTCTT | 82 |
| SEQ ID NO: 24 | GGAGGAGATGTAGAAATCAGCGGTAGGGGCTACACATTAATAGTATGGGCAGCGC | 53 |
| SEQ ID NO: 25 | ACGTTAAAGCTAATTAGCGCGGGTCACTAGTTCGGTAAAGGGGTTATGATGTGTTGTCTT | |
| SEQ ID NO: 26 | AAGAGACTACCGTGTTCGTGCAGTGAAATTCAGTACACTATGATCATTCCTGTTTCCACT | 119 |
| SEQ ID NO: 27 | ACGTCAATGTTAAACTGGTTCAATTACGCCCTGATACTCTTGACTACGACTCCGTACT | |
| SEQ ID NO: 28 | CCAGCGGCGGAGGATACAAAAAGTGGATAGGTTTCCGGGGAATGCAATGTTTATGGTTGG | 156.4 |
| SEQ ID NO: 29 | ATACGAAGGTGTAGTTAGCCGTTCTTAGAGTACAGACGTAATAAAGCATGTGTCCCTCAA | 87.1 |
| SEQ ID NO: 30 | GATCCACAGACTCAGCTTAGTCCGCTTCGTGATCTATCGCCGCCCATACCCCTATAGTA | |
| SEQ ID NO: 31 | GCAGATGTGGGACGACTCAACGATACACGGGGCACATGTCCTGCCCGCGATGTCAGCCG | 129 |

Binding studies were performed for the sequences in order to evaluate their affinity to the Dabigatran etexilate. By fixing the amount of Dabigatran etexilate beads and incubation with different concentrations of each aptamer sequence, the eluted DNA was monitored via fluorescence measurements. The dissociation constants ($K_d$s) were then calculated by non linear regression analysis of the saturation binding curve.

Application of the selected 60-mer aptamer in square wave voltammetry-based sensor: A thiol-modified form of the highest affinity sequence (SEQ ID NO: 1) which showed the lowest $K_d$ (5'HS-(CH2)6/TTCCGAGTTACATTCCCA-GTTTCAGAAGTCCCTACTTCATACCGACGATGCT-GAACT AAG-3') was immobilized on screen printed gold electrode by incubation of 1 μM solution of the aptamer in binding buffer on the gold surface for overnight (around 16 hours). After washing, the electrodes were incubated in 1 mM mercaptohexanol for blocking. The aptamer-modified electrode (aptasensor) was then incubated in different concentrations of dabigetran in binding buffer, spiked serum samples or other non specific proteins such as BSA. The sensor response was then measured using square wave voltammetry in 5 mM ferro/ferricyanide redox couple solution in 0.1 M PBS buffer pH 7.4.

Probing aptamer binding region: The aptamer sequence SEQ ID NO:1 which showed a $K_d$ of 47 nM was then subjected to mapping strategy to identify the binding region to Dabigatran etexilate. Though it has significant affinity, mapping the aptamer binding site and removing the non-essential nucleotides would tune-on it's the maximum affinity, potential sensing and therapeutic applications. Fluorescence off-on systems were designed for the identification of short sequence binding region. Duplexing of the desired aptamer sequence with 8-mer complementary sequences to bring the fluorophore and quencher to maximum close proximity prior target recognition was performed. The sequences used in this part are shown in Table 2. The binding region of the aptamer has been probed systematically by duplexing different parts of the aptamer with 8-mer sequences labeled FAM (6-Carboxyfluorescein) and Black Hole Quencher1 (BHQ1). The target induced DNA strand displacement was monitored by fluorescence signal after target recognition. The mfold software was used to find the possible secondary structures of the aptamer in the physiological condition to guide the design of duplexed sequences and truncation steps, shown in FIG. 1.

TABLE 2

Aptamer SEQ ID NO: 1 and complementary sequences used in this study

| Name | Sequence ( 5'-3") |
|---|---|
| SEQ ID NO:1 | TTCCGAGTTACATTCCCAGTTTCAGAAGTCCCTACTT CATACCGACGATGCTGAACTAAG |
| SEQ ID NO: 32 DBG1T1 | FAM- TACATTCCCAGTTTCAGAAGTCCCTACTTCAT ACCGACGATGCTGA |
| SEQ ID NO: 33 DBG1C1 | GGAATGTA-BHQ1 |
| SEQ ID NO: 34 DBG1T2 | ATTCCCAGTTTCAGAAGTCCCTACTTCATACCGACGA T |
| SEQ ID NO: 35 DBG1C2 | FAM-TGAAGTAGG |
| SEQ ID NO: 36 DBG1C3 | TCGTCGGTA BHQ-1 |

TABLE 2-continued

Aptamer SEQ ID NO: 1 and complementary sequences
used in this study

| Name | Sequence (5'-3") |
|---|---|
| SEQ ID NO: 37<br>DBG1T3 | GTTTCAGAAGTCCCTACTTCAAAC |
| SEQ ID NO: 38<br>DBG1C4 | FAM-TCTGAAAC |
| SEQ ID NO: 39<br>DBG1C5 | TAGGGACTBHQ1 |

FIG. 1 shows mfold predicted secondary structure of the 60-mer DBG aptamer of SEQ ID NO: 1. Three truncation steps conducted based on examination of three different potential target binding regions using the developed DNA displacement fluorescence assay. First truncation produced 52-mer variant, second truncation produced 38-mer variant, and the third truncation produced the 23-mer variant.

Three different variants of truncated aptamers have been achieved by following the described mapping strategy (FIG. 1). The first truncated aptamer has 52 nucleotide with four stem-loop/bulges obtained by slicing the five nucleotides from 5' end and last three nucleotide of the 3' end which are dangling in both ends (referred to as SEQ ID NO: 32). The binding region of the SEQ ID NO: 32 was tested by duplexing the 5' FAM (6-Carboxyfluorescein) labeled SEQ ID NO: 32 and 8-mer complementary DNA labelled with 3' BHQ1 (designated as SEQ ID NO: 33). There was only a background response when analyzing the affinity, leading to draw a conclusion that this part of the aptamer does not contain the binding region. Based on this conclusion, the second copy was designed, which consist of 38 nucleotides, 10 to 48 from 5'- end of the original aptamer with three loops/bulges referred to as SEQ ID NO: 34. This sequence was duplexed with equimolar concentrations of aptamer and the corresponding complementary sequences labelled with FAM and BHQ1 at the region close to 3'- end of this sequence (designated as SEQ ID NO: 35 and SEQ ID NO: 36). The incubation with DBG resulted in very high sensitivity response and the calculated KD was 1 nM. More aggressive truncation resulted in the third and last 23-mer truncated copy of the aptamer. This resulted in the middle region of the aptamer from 17 to 40 from the 5'- end with two stem-loop/bulge referred to as SEQ ID NO: 37. The binding ability was conducted as the 38-mer aptamer but with different complementary sequences targeting nucleotides close to 5'- end of this sequence (designated as SEQ ID NO: 38, SEQ ID NO: 39). The 23-mer aptamer was unable to recognize the target based on the affinity studies. Therefore, no further truncation steps were conducted.

DNA Displacement Fluorescence Assay: In the ssDNA strand displacement induced fluorescence assay, equimolar concentration of 50 nM truncated aptamer, FAM and BHQ1 labelled complementary sequences were mixed in the binding buffer. The mixture was kept in a beaker containing hot water (90° C.) in a dark room, to form desired dsDNA duplex. The solution in the hot water was allowed to cool slowly to room temperature (for 3 h). The slow cooling process would form perfect dsDNA duplex bearing the fluorophore and quencher close to each other (this was indicated from the fluorescence quenching experiments). The affinity of each truncated aptamer was evaluated by monitoring the increase in fluorescence intensity, after 45 min incubation of the hybridized duplex with different concentrations of DBG in the range 0 to 250 nM. Each sample was excited at 485 nm and the fluorescence intensity was recorded at 515 nm. The change in the fluorescence intensity of the duplexed aptamers was plotted against the corresponding DBG concentrations to obtain the saturation binding curve. The affinity of the each aptamer for DBG was calculated by fitting the saturation curve by non-linear regression analysis using Prism graph pad.

Cross reactivity and real sample testing: The selectivity of the 38-mer aptamer for DBG was tested using a number of potential biological interfering molecules. The selectivity of the aptamer binding was tested at 50 nM concentration of DBG, 17-β-estradiol, vitamin D3, and progesterone. The percentage change in the fluorescence intensity (using the DNA displacement fluorescence assay described above) upon incubation with different targets represents the cross reactivity of the truncated aptamer. Application of the developed aptasensor using the truncated 38-mer was validated using the DBG spiked in diluted plasma/serum (1:100). A calibration plot was generated by plotting known concentrations of DBG in sensor duplex solutions and their corresponding fluorescence. Then, different concentrations (5, 10 and 50 nM) of DBG were spiked plasma/serum, incubated with the aptasensor, and the corresponding fluorescence intensity changes were recorded. The recovery amount of DBG was calculated from the increase in the fluorescence and a comparison made against the calibration curve.

Results and Discussion

Figure 2A:
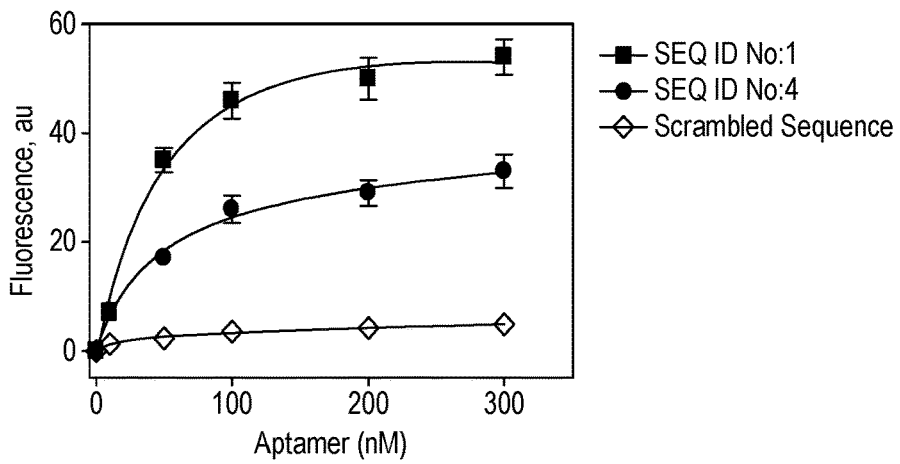
FIGS. 2A, 2B and 2C Binding affinity graphs for the selected 60-mer aptamers against Dabigatran etexilate.
Figure 2B:
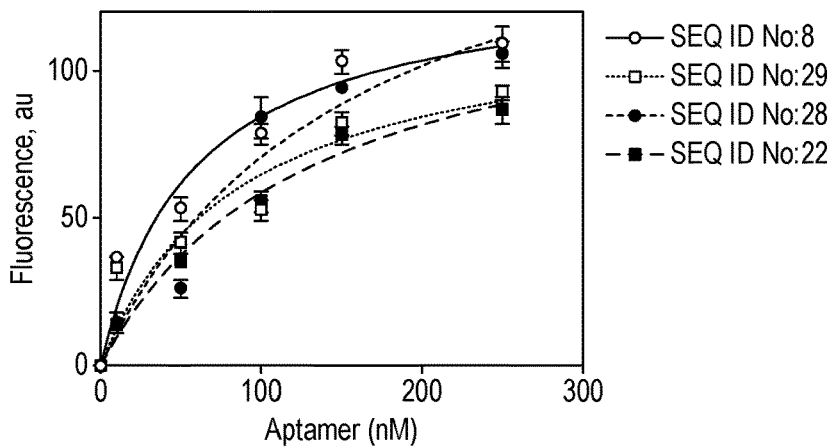
Figure 2C:
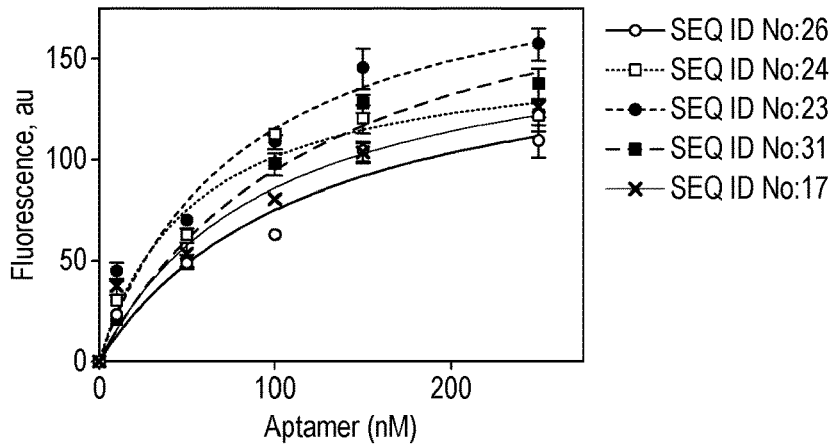

The selection of the 60-mer aptamers against Dabigatran etexilate was performed using SELEX. Several sequences were obtained as shown in Table 1. The $K_d$s of the selected sequences were determined using fluorescence-based binding assay. The saturation curves of some of the selected aptamers are shown in FIGS. 2A, 2B and 2C. From the non linear regression fitting of the curves, the $K_d$s were calculated to be 47 to 312 nM indicating high affinity of the new selected aptamers to dabigetran. The aptamer sequences which showed the highest affinity (SEQ ID NO: 1 and SEQ ID NO: 4) were then tested in an electrochemical biosensor platform.

Figure 3A:
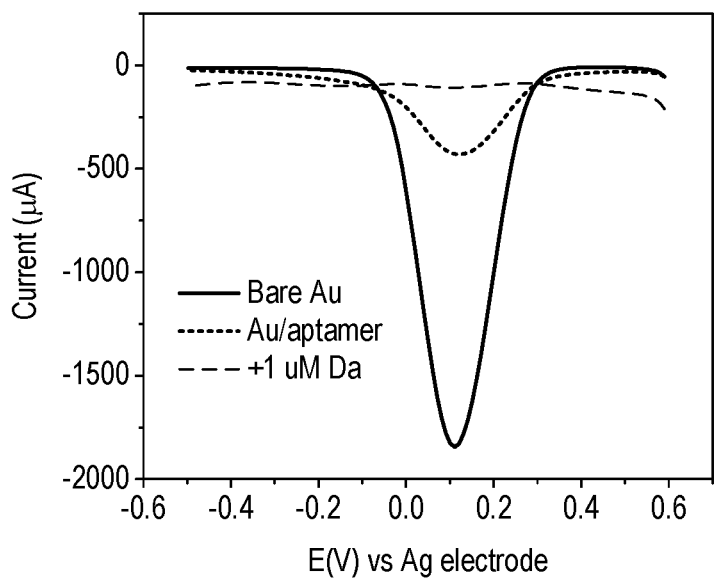
FIG. 3A square wave voltammograms of the bare gold electrodes before (black), after immobilization of the aptamer (red) and after incubation with dabigetran (blue).

Thiolated aptamer sequences were attached to gold electrode surface by self assembly mono layer formation and then the surface was blocked with mercaptohexanol to eliminate the adsorption of the DNA on the free gold area and reduces the steric hindrance effect. FIG. 3A shows the SWV reduction peaks of the electrodes at different steps in ferro/ferricyanide redox solution.

Figure 3B:
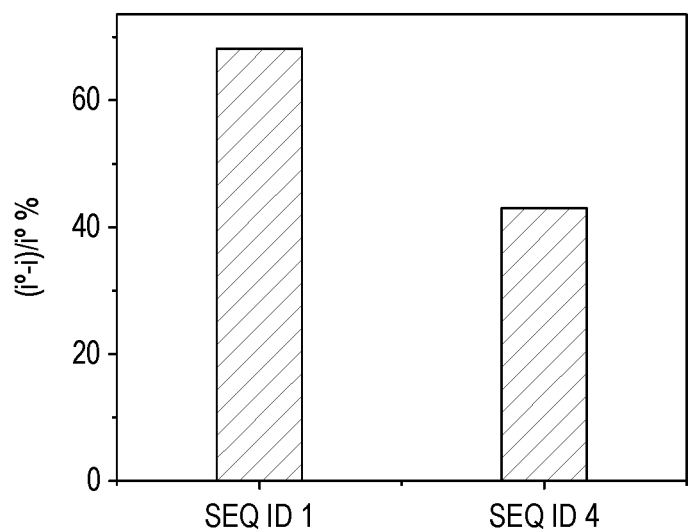
FIG. 3B comparison of two sensor response prepared using the aptamer SEQ ID NO: 1 (the large value in the bar graph) and the aptamer SEQ ID NO: 4 (the small value).

FIG. 3A square wave voltammograms of the bare gold electrodes before, after immobilization of the aptamer and after incubation with dabigetran. FIG. 3B show the comparison of two sensors response prepared using the aptamer SEQ ID NO: 1 (the large value in the bar graph) and the aptamer SEQ ID NO: 4 (the small value). After the immobilization of the aptamer, the peak current significantly decreased compared to the bare gold electrode. This is attributed to the negatively charged phosphate backbone of the DNA, this repels the redox anions from the surface. However, after the incubation with the dabigetran, we observed a further decrease in the peak current. We believe that this decrease is likely to be due to the conformational change within the aptamer sequence upon binding with the dabigetran molecules. Moreover, the presence of dabigetran molecules on the surface after binding retards the access of the redox molecules to the surface and thus, diminishes the reduction current. Two high affinity sequences were tested (SEQ ID NO: 1 and SEQ ID NO: 4) and sensor response (the change in the reduction current) was monitored in each case. It was observed that the aptamer SEQ ID NO: 1 showed higher sensor response, therefore, it was chosen for further testing.

Figure 4A:
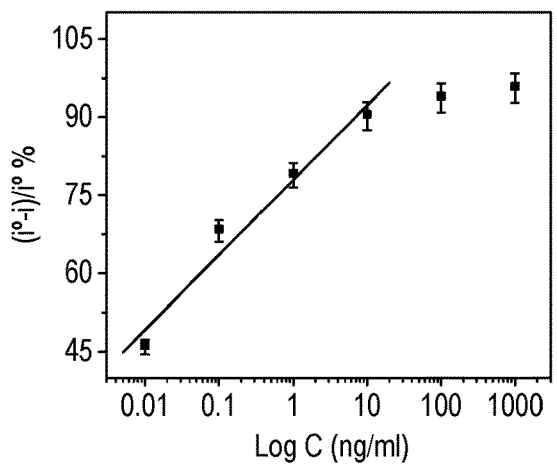
FIG. 4A calibration plot of the aptasensor prepared using aptamer SEQ ID NO: 1.
Figure 4B:
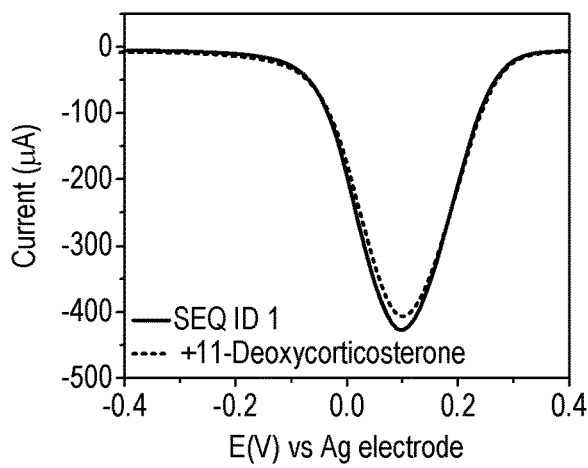
FIG. 4B voltammograms of the aptasensor before and after incubation with nonspecific analyte.
Figure 4C:
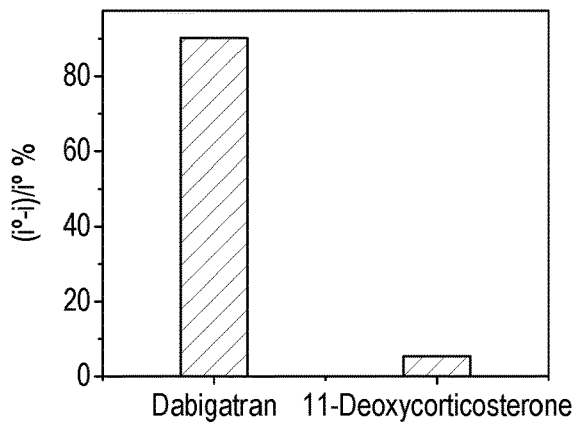
FIG. 4C chart bar plot of the sensor response to the specific and nonspecific analytes.

FIG. 4 (A) calibration plot of the aptasensor prepared using aptamer SEQ ID NO: 1. (B) voltammogram of the aptasensor before and after incubation with nonspecific analyte. (C) chart bar plot of the sensor response to the specific and nonspecific analytes. The detection experiments showed linear response as shown in the calibration plot (FIG. 4A) from 10 pg/ml to 10 ng/ml indicating good sensitivity of the aptasensor. The selectivity of the aptasensor was also investigated by incubating the sensor with 11-deoxy corticosterone. As shown in FIG. 4B, the SWV signal did not exhibit any significant change after incubation with 11-deoxy corticosterone. FIG. 4C, shows the non significant response of the aptasensor to the nonspecific analyte compared with the high sensor response to dabigetran indicating the high selectivity of the sensor.

Mapping designs of the binding region and their outcomes: Unlike previous studies, the binding region mapping protocol proposed here relies on the aptamer's solution free-state under common biological conditions, pH 7.5, 2 mM $MgCl_2$ and 150 mM NaCl. Although the secondary structure of the 60-mer aptamer is used to assist visualizing the process, linear form of the aptamer can be used with successful implementation of the strategy. As shown in FIG. 1, we begin to examine nucleotides close to 5'- end of the random core sequences by generating the 52-mer sequence with four loop/bulges obtained by trimming the five nucleotides from 5'- end and the last three nucleotide of the 3'- end (SEQ ID NO: 32). These nucleotides are dangling in both sides of the aptamer and are less probable to form the binding region. 3'-BHQ1 8-mer complementary sequence was hybridized to the 5'-FAM 52-mer aptamer at nucleotides numbers 1 to 8. There is no change in fluorescence intensity when DBG was incubated at increasing concentrations. This result indicates that target-induced conformational change occurs in a region far from the examined bases, leading the duplexed sequence to remain hybridized.

Figure 5A:
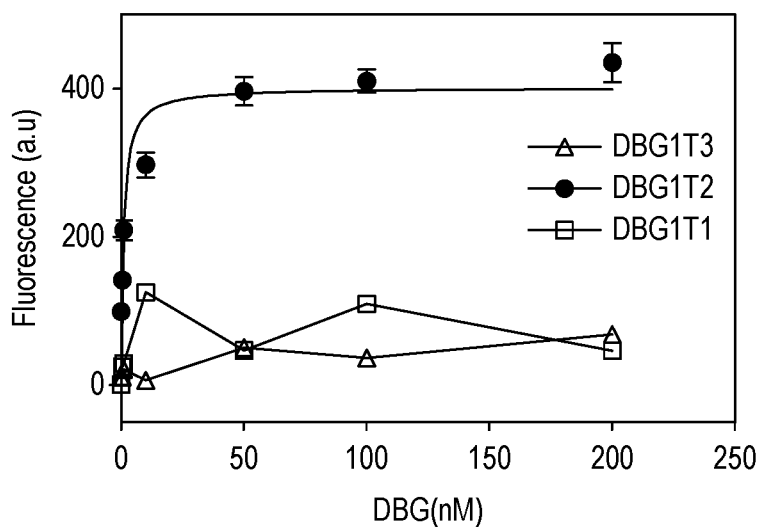
FIG. 5A: binding isotherms for the examination of truncated aptamers with the fluorescence displacement assay. The affinity of the three aptamer variants for DBG was calculated by fitting the saturation curves by non-linear regression analysis using Prism graph pad.
Figure 5B:
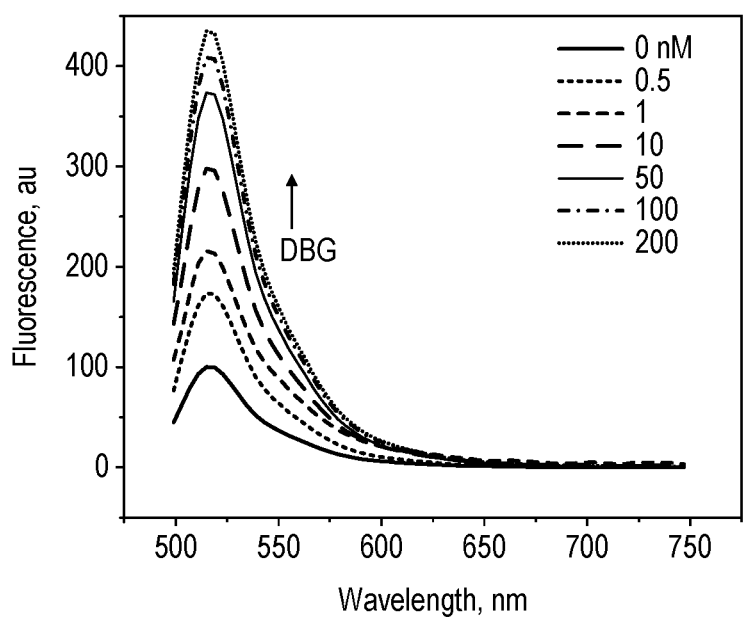
FIG. 5B: fluorescence spectra of the 38-mer aptamer duplexed with the complementary sequences labeled with fluorescein and BHQ1 and incubated with increasing concentration of DBG.

Next, a 38-mer aptamer was designed to contain nucleotides from 10 to 48 from 5'- end of the parent aptamer with three stem-loops/bulges (SEQ ID NO: 34), as shown in FIG. 1. This aptamer was duplexed with two 8-mer complementary sequences containing the FAM and BHQ1 in nucleotides close to the 3'- end since the first examination did not result in DNA displacement when DBG was recognized. The complementary sequences were hybridized with nucleotides number 16 to 32 of the truncated aptamer, in an extent where the fluorophore and quencher are brought to maximum proximity, refer to Table 1 for further details. As shown in FIG. 5, the incubation with increasing concentrations of DBG resulted in a very high sensitivity response, showing a saturation behavior at 50 nM of DBG concentration. The calculated $K_D$ of this variant was 1 nM. In fact the calculated binding affinity is 47 fold higher than the original full length (60-mer) probe. This finding indicates that a significant target-induced conformational change occurred within the truncated 38-mer sequence, resulting in the displacement of at least one of the 8-mer complementary sequences.

FIG. 5 A: binding isotherms for the examination of truncated aptamers with the fluorescence displacement assay. The affinity of the three aptamer variants for DBG was calculated by fitting the saturation curves by non-linear regression analysis using Prism graph pad. B: fluorescence spectra of the 38-mer aptamer duplexed with the complementary sequences labeled with fluorescein and BHQ1 and incubated with increasing concentration of DBG.

Thus far, it is not clear if additional truncation of the aptamer sequence will result in further refinement and narrowed isolation of the binding region. Since the second truncation and duplexation targeted nucleotides close to the 3'- end of the 38-mer aptamer, we examined the involvement of the nucleotides close to the 5'- end by duplexing bases from 21 to 36 of the parent aptamer with 8-mer complementary sequences labelled with the fluorophore and quencher in the same fashion as described above with the 38-mer. Dually, the 38-mer aptamer was further truncated to generated a 23-mer variant that contains the middle region of the parent aptamer with two stem-loop/bulge structures (SEQ ID NO: 37). As shown in FIG. 5, only back ground response can be seen when increasing concentrations of the DBG were incubated with the 23-mer aptamer.

Such observation can be explained by the considering the following scenarios: 1) the binding bucket could be within the duplexed nucleotides which could potentially altered the 3D structure and disabled target recognition, 2) truncating the 38-mer to generate the shorter version removed some of the bases directly involved in the target binding and 3) the third truncation step could have resulted in the removal of some supporting nucleotides that maintain the desired structure of the binding region. In spite of these possible explanations, our approach has identified the binding region with the required nucleotides to support the desired 3D structure. Additionally, the optimum duplexation design that leads to sequence displacement was achieved with the 38-mer aptamer, which allows researchers to implement the reported molecular architecture in various sensors platforms.

CD Studies

Figure 6A:
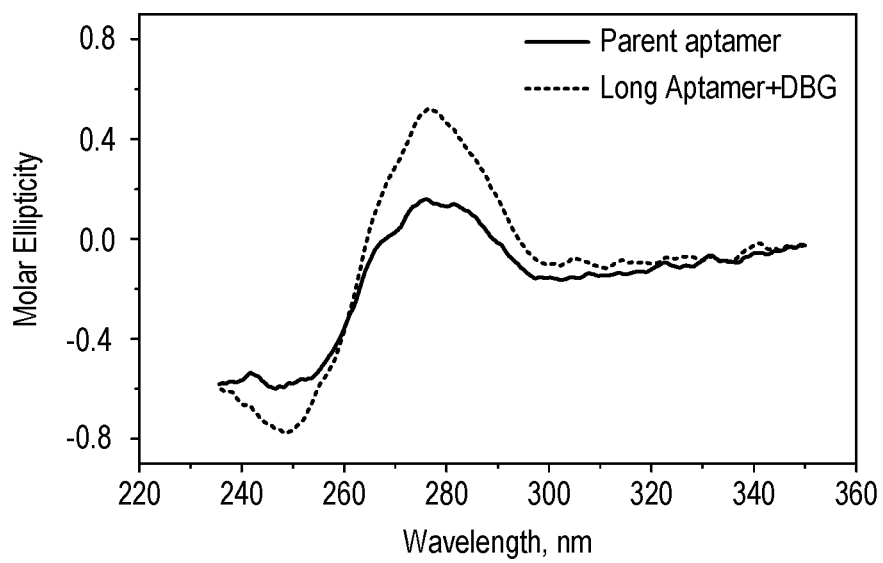
FIG. 6A CD spectroscopy analysis of 2 µM concentration of the parent DBG aptamer and the truncated DBG1 T2 aptamer FIG. 6B before and after incubation with 5 µM concentration of the target molecules.
Figure 6B:
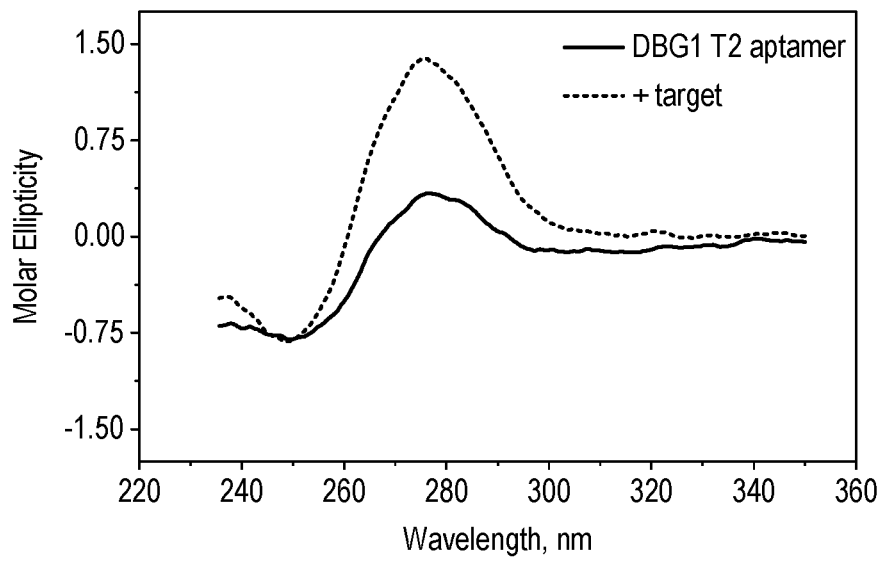

To explore the possibility that nucleotides flanked to binding region could perturb the 3D structure or conformational change of the core region and thereby lead to enhancement in the interaction with the target, we probed 3D structures via CD spectroscopy (Chang et al., 2012). This technique can provide in-solution characterization of the aptamer folding on its target. It was previously used to evaluated and compare many aptamer candidates for small targets after SELEX process. FIG. 6A CD spectroscopy analysis of 2 μM concentration the parent DBG aptamer and the truncated DBG1 T2 aptamer FIG. 6B before and after incubation with 5 μM concentration of the target molecules analysis. As shown in FIGS. 6A and 6B, there is no significant difference in the CD spectra of the parent 60-mer aptamer and the truncated 38-mer variant. Upon incubation with the target at a concentration of 5 μM, the truncated sequence showed remarkably more sensitive response than the parent aptamer. In fact, the 38-mer shows at least 4-folds higher ellipticity signals compared to the parent sequence. Consistent with previous reports, it is likely that the non-binding nucleotides in the 60-mer aptamer could impose steric effect that prevents maximum structural switch when the target is recognized. This result supports our observation that the 38-mer truncated aptamer is a better binder than the parent aptamer, with a $K_D$ value of 1 nM vs. 47 nM for the 60-mer aptamer.

Figure 7A:
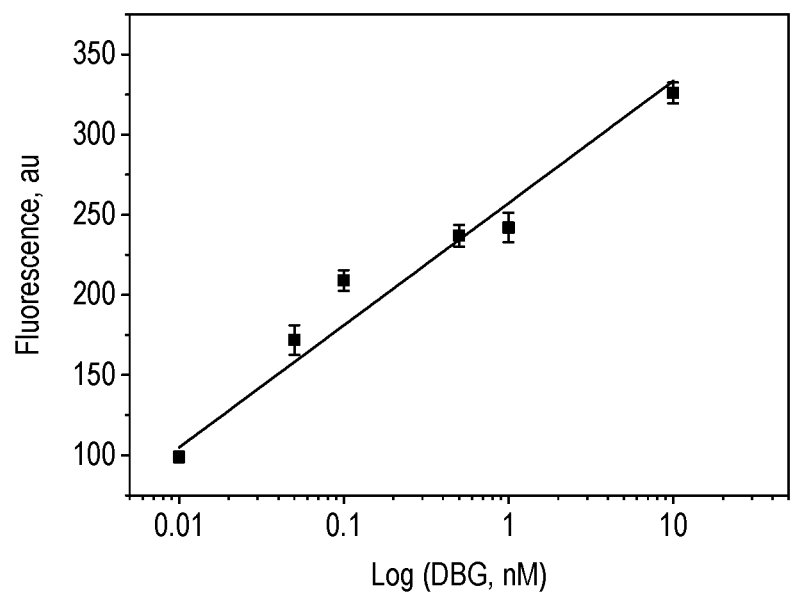
FIG. 7A: calibration curve of fluorescence signal-on sensor using the 38-mer aptamer plotted as the change in the fluorescence intensity versus logarithm of DBG concentration.
Figure 7B:
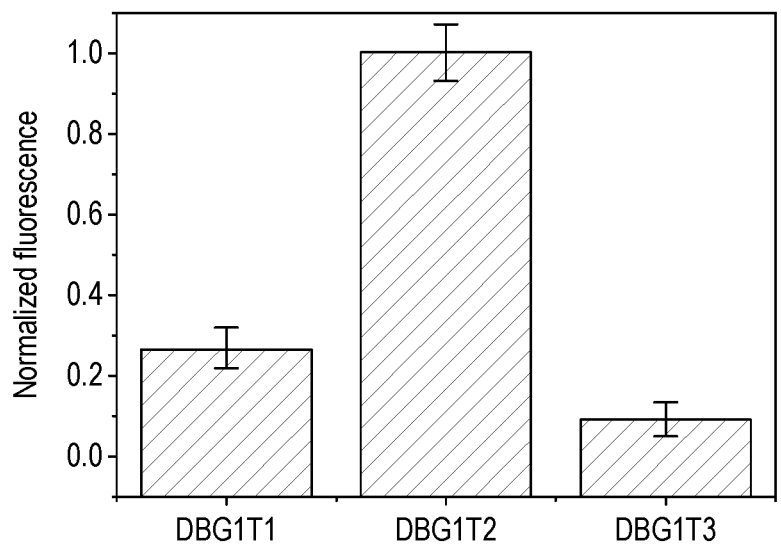
FIG. 7B: control experiments showing relative change in the fluorescence intensity of truncated aptamers obtained from various regions of the original aptamer, 52-mer (SEQ ID NO: 32), 38-mer (SEQ ID NO: 34) and 23-mer (SEQ ID NO: 37). DBG1 T2 (SEQ ID NO: 34) shows the largest increase in the fluorescence intensity in the presence of 50 nM DBG concentration.

Dabigetran Aptasensor Based on Fluorescence Displacement:

Having identified the binding region of DBG and the optimum design for target recognition induced sequence displacement; we proceed to establish a sensitive signal-on fluorescence sensor. DBG was titrated with the 38-mer tripartite fluorescence-quenching dsDNA duplex assembly and the change in fluorescence was recorded. As can be seen in FIG. 7A, a linear relation between the change in fluorescence and target concentration was established. The lowest detected concentration of DBG is 1 nM (defined as S/N>3) with an excellent linearity ($R^2$=0.98) and a wide analytical window. The established sensor is highly robust as the error bars in FIG. 7A represent the standard deviation of the mean of three independent experiments starting from 38-mer duplex formation. To verify that the sensor signals arose from specific DBG recognition, we conducted two sets of control experiments. As shown in FIG. 7B, 50 nM DBG solution was incubated with the three different duplexation designs generated for the different aptamer variants (52-mer, 38-mer, and 23-mer). The control experiments lack significant change in fluorescence response when the DBG was incubated and show that indeed the signal arose from specific conformational change of the 38-mer aptamer that lead to displacement of at least one 8-mer complementary sequence. It is important to note that the resolved nM analytical window is highly relevant to the potential application of the developed sensor as a quick analytical tool. It can provide guidance for treatment of cases of massive bleeding or emergency surgery. It was found that there is a strong correlation between the rate of major bleeding and plasma concentration of DBG (Moore et al., 2014). The approved FDA DBG level is 150 mg strength and the therapeutic level of DBG is proposed to be within the range from 76.4 to 318.6 nM (Stangier and Clemens, 2009). This shows that the constructed sensor falls within the expected biological range of DBG. Therefore, the developed signal-on sensor could be successfully utilized for the detection of DBG in point-of-care testing and monitoring applications. FIG. 7 A: calibration curve of fluorescence signal-on sensor using the 38-mer aptamer plotted as the change in the fluorescence intensity versus logarithm of DBG concentration. B: control experiments showing relative change in the fluorescence intensity of truncated aptamers obtained from various regions of the original aptamer, 52-mer (SEQ ID NO: 32), 38-mer (SEQ ID NO: 34) and 23-mer (SEQ ID NO: 37). DBG1 T2 (SEQ ID NO: 34) shows the largest increase in the fluorescence intensity in the presence of 50 nM DBG concentration. No significant change in the fluorescence intensity of other truncated aptamers in the presence of 50 nM DBG concentration confirming the specificity of the sensor signals. Error bars represent standard deviation of three independent experiments.

Figure 8A:
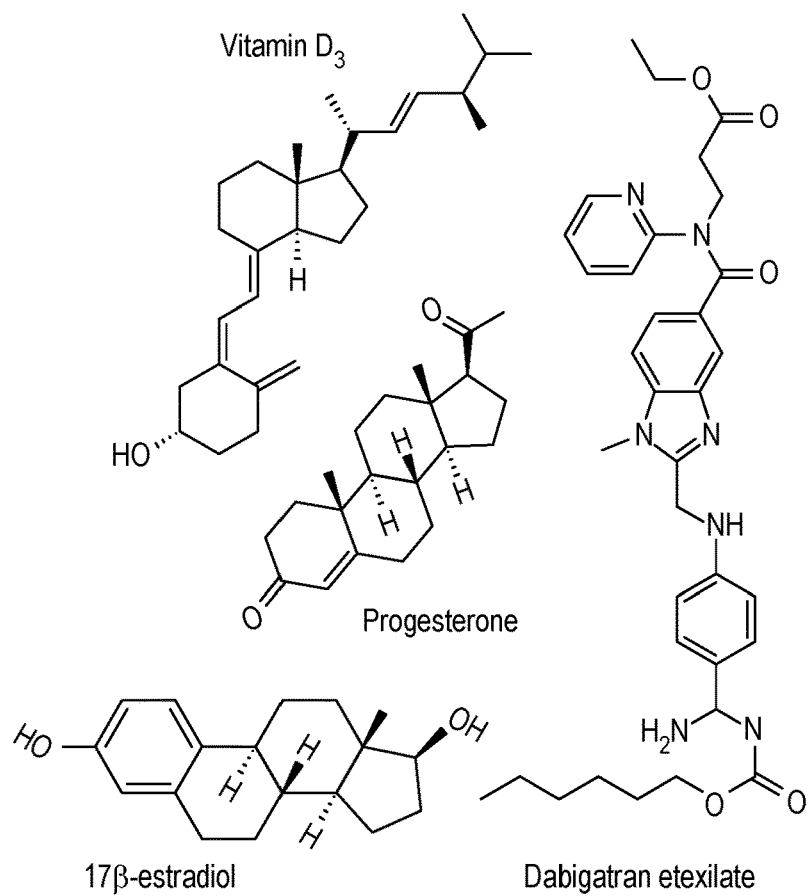
FIG. 8A: molecular structures of DBG and interfering molecules used to examine the selectivity of the signal-on fluorescence sensor.
Figure 8B:
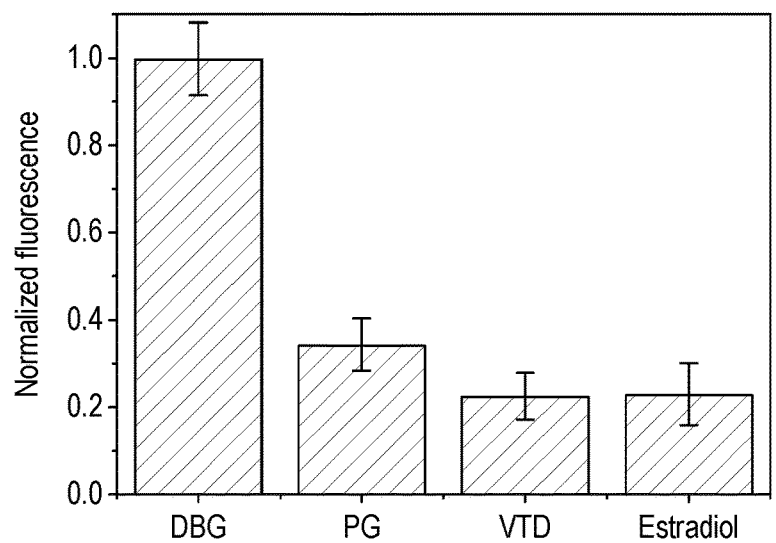
FIG. 8B: cross reactivity of the 38-mer aptamer based sensor in the presence of 50 nM DBG concentration and other interfering molecules. Error bars represent standard deviations of three independent experiments.

Selectivity of DBG fluorescence displacement sensor and application in biological samples: FIG. 8A: molecular structures of DBG and interfering molecules used to examine the selectivity of the signal-on fluorescence sensor. FIG. 8B: cross reactivity of the 38-mer aptamer based sensor in the presence of 50 nM DBG concentration and other interfering molecules. Error bars represent standard deviations of three independent experiments. The selectivity of the 38-mer duplex displacement format to DBG was examined by exposing the sensor to other compounds likely to be encountered when DBG is detected in biological samples; their molecular structures are shown in FIG. 8A. As shown in FIG. 8B, there is no significant increase in the fluorescence intensity with these molecules compared with the high response obtained when the 38-mer duplex is disassembled upon DBG recognition, indicating the selectivity of the developed aptasensor to the target.

TABLE 3

Application of 38-mer aptamer in the detection of DBG from plasma/serum samples.

| Spiked amount (nM) | Found amount (nM) | % Recovery | Standard Error |
|---|---|---|---|
| 0.1 | 0.0985 | 98.5 | ±6.4 |
| 0.5 | 0.504 | 100.85 | ±6.8 |
| 10 | 10.24 | 102.4 | ±9.2 |

Finally, the performance of the 38-mer aptamer based signal-on sensor in real plasma/serum samples was tested. Three different DBG concentrations were spiked in plasma/serum matrix and incubated with the duplex form of the 38-mer aptamer. Fluorescence change was recorded and compared against a calibration curve made using the same sample components. As shown in Table 3, excellent recovery percentages of DBG from plasma/serum samples were calculated without significant interference from other components in the sample. The result suggests that the developed sensor can be applied to detect DBG in real samples.

TABLE 4

Shows only the sequences without fluorescein and BHQ1:

| Name | Sequence ( 5'-3") |
|---|---|
| SEQ ID NO: 1 | TTCCGAGTTACATTCCCAGTTTCAGAAGTCCCTACTTCATACCGACGATGCTGAACTAAG |
| SEQ ID NO: 32 DBG1T1 | TACATTCCCAGTTTCAGAAGTCCCTACTTCATACCGACGATGCTGA |
| SEQ ID NO: 33 DBG1C1 | GGAATGTA |
| SEQ ID NO: 34 DBG1T2 | ATTCCCAGTTTCAGAAGTCCCTACTTCATACCGACGAT |
| SEQ ID NO: 35 DBG1C2 | TGAAGTAGG |
| SEQ ID NO: 36 DBG1C3 | TCGTCGGTA |
| SEQ ID NO: 37 DBG1T3 | GTTTCAGAAGTCCCTACTTCAAAC |
| SEQ ID NO: 38 DBG1C4 | TCTGAAAC |
| SEQ ID NO: 39 DBG1C5 | TAGGGACT |

What is claimed is:

1. A method of analyzing a drug concentration in human serum, comprising:

selecting a single stranded oligonucleotide 60 mer aptamer sequence comprises a sequence selected from the sequences of SEQ ID Nos: 1-31 using a systemic evolution of ligands by exponential treatment (selex) method for the drug;

evaluating the binding affinity of the single stranded oligonucleotide 60 mer aptamer sequence comprises a sequence selected from the sequences of SEQ ID Nos: 1-31 using a fluorescence assay;

immobilizing a highest affinity single stranded oligonucleotide 60 mer aptamer sequence comprises a sequence selected from the sequences of SEQ ID Nos: 1-31 on gold electrode; and determining a binding region for the highest affinity single stranded oligonucleotide 60 mer aptamer comprises a sequence selected from the sequences of SEQ ID Nos: 1-31 on the drug.

2. The method of claim 1, further comprising;
mapping of the binding region within the said aptamer to the drug was performed using a truncated sequence and two complimentary sequences of the said aptamer labelled with a fluorophore and a quencher.

3. The method of claim 2, further comprising;
constructing a turn-on fluorescence sensor by selecting a truncated 38-mer sequence showing higher affinity than the said aptamer.

4. The method of claim 3, further comprising;
detecting the drug in a serum using the turn-on fluorescence sensor using the selected truncated 38-mer sequence and optimizing a drug dose to a patient based on the feedback.

5. The method of claim 1, wherein the drug is a Dabigatran etexilate.

6. The method of claim 1, wherein the 60-mer aptamers comprises a sequence selected from the sequences of SEQ ID Nos: 1-31 are SEQ ID No:1-31.

7. The method of claim 2, wherein the truncated sequences and the complimentary sequences are SEQ ID NO: 32-39.

8. A method of analyzing a drug concentration in human plasma, comprising:
selecting a single stranded oligonucleotide 60 mer aptamer sequence using a systemic evolution of ligands by exponential treatment (selex) method for the drug, wherein the drug is a Dabigatran etexilate;
evaluating the binding affinity of the single stranded oligonucleotide 60 mer aptamer sequence using a fluorescence assay;
immobilizing a highest affinity single stranded oligonucleotide 60 mer aptamer sequence on gold electrode, wherein the highest affinity single stranded oligonucleotide 60 mer aptamer sequence is SEQ ID NO:1;
determining a binding region for the highest affinity single stranded oligonucleotide 60 mer aptamer on the drug;
mapping of the binding region within the said aptamer to the drug was performed using a truncated sequence and a complimentary sequence of the said aptamer and labelled with a fluorophore and a quencher; and
constructing a turn-on fluorescence sensor by selecting a truncated 38-mer sequence showing the higher affinity than the said aptamer.

9. The method of claim 8, further comprising;
detecting the drug in a serum using the turn-on fluorescence sensor selecting the truncated 38-mer sequence and optimizing a drug dose to a patient based on the feedback.

10. The method of claim 9, wherein the truncated sequence and the complimentary sequence are SEQ ID NO: 32-39.

* * * * *

SEQUENCE LISTING

<160> NUMBER OF SEQ ID NOS: 39

<210> SEQ ID NO 1
<211> LENGTH: 60
<212> TYPE: DNA
<213> ORGANISM: Artificial Sequence -continued

```
<220> FEATURE:
<223> OTHER INFORMATION: Aptamer

<400> SEQUENCE: 1
ttccgagtta cattcccagt ttcagaagtc cctacttcat accgacgatg ctgaactaag      60

<210> SEQ ID NO 2
<211> LENGTH: 60
<212> TYPE: DNA
<213> ORGANISM: Artificial Sequence
<220> FEATURE:
<223> OTHER INFORMATION: Aptamer

<400> SEQUENCE: 2
ggatccagag tgaaggataa agccgtatat gattattgat ccgaccccac catagtacgt      60

<210> SEQ ID NO 3
<211> LENGTH: 60
<212> TYPE: DNA
<213> ORGANISM: Artificial Sequence
<220> FEATURE:
<223> OTHER INFORMATION: Aptamer

<400> SEQUENCE: 3
ggaggtgctg tgactcagta gctctgttag tttgtatggc tacatgtgtg agggtgatac      60

<210> SEQ ID NO 4
<211> LENGTH: 60
<212> TYPE: DNA
<213> ORGANISM: Artificial Sequence
<220> FEATURE:
<223> OTHER INFORMATION: Aptamer

<400> SEQUENCE: 4
acagccaaga gtgcgatgta ttaatcatta acaaaactgc cggtgcatgc cctccgacca      60

<210> SEQ ID NO 5
<211> LENGTH: 60
<212> TYPE: DNA
<213> ORGANISM: Artificial Sequence
<220> FEATURE:
<223> OTHER INFORMATION: Aptamer

<400> SEQUENCE: 5
agtgaacgga cgatcaaaga caacatatgg tccgaatttt gaacaggtcg ttggggatgg      60

<210> SEQ ID NO 6
<211> LENGTH: 60
<212> TYPE: DNA
<213> ORGANISM: Artificial Sequence
<220> FEATURE:
<223> OTHER INFORMATION: Aptamer

<400> SEQUENCE: 6
cgattaaagc atataatagt agtatccagg gtgataatga tgatgcttcg aggcagtagg      60

<210> SEQ ID NO 7
<211> LENGTH: 59
<212> TYPE: DNA
<213> ORGANISM: Artificial Sequence
<220> FEATURE:
<223> OTHER INFORMATION: Aptamer

<400> SEQUENCE: 7
gaataacgag gagtgtccgg gataggaagt aatcattctt acacattcgc accatgtca       59
```

```
<210> SEQ ID NO 8
<211> LENGTH: 59
<212> TYPE: DNA
<213> ORGANISM: Artificial Sequence
<220> FEATURE:
<223> OTHER INFORMATION: Aptamer

<400> SEQUENCE: 8
aaccggccct ccgatgatta gctaactgtt tgcggtctaa tttagcgttt gttctgtgc      59

<210> SEQ ID NO 9
<211> LENGTH: 60
<212> TYPE: DNA
<213> ORGANISM: Artificial Sequence
<220> FEATURE:
<223> OTHER INFORMATION: Aptamer

<400> SEQUENCE: 9
gaaccctggc gtgccctata tttttcaaat tgtgatgtct ttagggcctg ataaccgaat     60

<210> SEQ ID NO 10
<211> LENGTH: 60
<212> TYPE: DNA
<213> ORGANISM: Artificial Sequence
<220> FEATURE:
<223> OTHER INFORMATION: Aptamer

<400> SEQUENCE: 10
tgaataacga ggagtgtccg ggataggaag taatcattct tacacattcg caccatgtca    60

<210> SEQ ID NO 11
<211> LENGTH: 60
<212> TYPE: DNA
<213> ORGANISM: Artificial Sequence
<220> FEATURE:
<223> OTHER INFORMATION: Aptamer

<400> SEQUENCE: 11
aaatatcggt aagggtgagt actgtctagc gccccattga tgtataggtc cccagttagg    60

<210> SEQ ID NO 12
<211> LENGTH: 60
<212> TYPE: DNA
<213> ORGANISM: Artificial Sequence
<220> FEATURE:
<223> OTHER INFORMATION: Aptamer

<400> SEQUENCE: 12
tgttaagaag accggtggag ccgccaatca atagttcaat gcctgagagt gttacgaggg    60

<210> SEQ ID NO 13
<211> LENGTH: 58
<212> TYPE: DNA
<213> ORGANISM: Artificial Sequence
<220> FEATURE:
<223> OTHER INFORMATION: Aptamer

<400> SEQUENCE: 13
tcaagtatag tactaacaaa caggggatt gacatcaagt gtgataggt aagtatga        58

<210> SEQ ID NO 14
<211> LENGTH: 60
<212> TYPE: DNA
<213> ORGANISM: Artificial Sequence
<220> FEATURE:
<223> OTHER INFORMATION: Aptamer
```

<400> SEQUENCE: 14
gtaatgcgcg taccgtgcga aggaagtcct cccgggtcag tgtgagtggt tttgtccttt    60

<210> SEQ ID NO 15
<211> LENGTH: 57
<212> TYPE: DNA
<213> ORGANISM: Artificial Sequence
<220> FEATURE:
<223> OTHER INFORMATION: Aptamer

<400> SEQUENCE: 15
ccagtaccga ttgttgtctt atgtgatgta tcacgtgcgt atggatgtaa atgccca    57

<210> SEQ ID NO 16
<211> LENGTH: 59
<212> TYPE: DNA
<213> ORGANISM: Artificial Sequence
<220> FEATURE:
<223> OTHER INFORMATION: Aptamer

<400> SEQUENCE: 16
cgatgaaaag gaattcttgt agttatgggc ttcatcatgt gctaatggag ggtgcgtgg    59

<210> SEQ ID NO 17
<211> LENGTH: 58
<212> TYPE: DNA
<213> ORGANISM: Artificial Sequence
<220> FEATURE:
<223> OTHER INFORMATION: Aptamer

<400> SEQUENCE: 17
tcgtatagct agccctcaat gcagtgacct cggtaaacga aggcttctac aatgtggt    58

<210> SEQ ID NO 18
<211> LENGTH: 59
<212> TYPE: DNA
<213> ORGANISM: Artificial Sequence
<220> FEATURE:
<223> OTHER INFORMATION: Aptamer

<400> SEQUENCE: 18
gcagatgtgg gacgactcaa cgatacacgg ggcacatgtc ctgcccgcga tgtcagccg    59

<210> SEQ ID NO 19
<211> LENGTH: 60
<212> TYPE: DNA
<213> ORGANISM: Artificial Sequence
<220> FEATURE:
<223> OTHER INFORMATION: Aptamer

<400> SEQUENCE: 19
catcgagagg tagggtcatt agcaggacga gagcggtcta tattctgggc ggatcgctat    60

<210> SEQ ID NO 20
<211> LENGTH: 59
<212> TYPE: DNA
<213> ORGANISM: Artificial Sequence
<220> FEATURE:
<223> OTHER INFORMATION: Aptamer

<400> SEQUENCE: 20
aaagagacat tcagttataa aagtggtcac cgggatattt tgcaaagatc gactaaggt    59

<210> SEQ ID NO 21

```
<211> LENGTH: 60
<212> TYPE: DNA
<213> ORGANISM: Artificial Sequence
<220> FEATURE:
<223> OTHER INFORMATION: Aptamer

<400> SEQUENCE: 21
tgagtcaggt tgttggacga aatgtagata tgtgtcatac cgacccgctg tcccgcgtta      60

<210> SEQ ID NO 22
<211> LENGTH: 60
<212> TYPE: DNA
<213> ORGANISM: Artificial Sequence
<220> FEATURE:
<223> OTHER INFORMATION: Aptamer

<400> SEQUENCE: 22
acggggacgt tgagccgatc gactaaataa cgtcacgata ccgtagtagg gcggatattt      60

<210> SEQ ID NO 23
<211> LENGTH: 60
<212> TYPE: DNA
<213> ORGANISM: Artificial Sequence
<220> FEATURE:
<223> OTHER INFORMATION: Aptamer

<400> SEQUENCE: 23
cgaatagggg aggtgcatca cagtataccc ttacgagcgc atttagtagt gttaagtctt      60

<210> SEQ ID NO 24
<211> LENGTH: 55
<212> TYPE: DNA
<213> ORGANISM: Artificial Sequence
<220> FEATURE:
<223> OTHER INFORMATION: Aptamer

<400> SEQUENCE: 24
ggaggagatg tagaaatcag cggtaggggc tacacattaa tagtatgggc agcgc           55

<210> SEQ ID NO 25
<211> LENGTH: 60
<212> TYPE: DNA
<213> ORGANISM: Artificial Sequence
<220> FEATURE:
<223> OTHER INFORMATION: Aptamer

<400> SEQUENCE: 25
acgttaaagc taattagcgc gggtcactag ttcggtaaag gggttatgat gtgttgtctt      60

<210> SEQ ID NO 26
<211> LENGTH: 60
<212> TYPE: DNA
<213> ORGANISM: Artificial Sequence
<220> FEATURE:
<223> OTHER INFORMATION: Aptamer

<400> SEQUENCE: 26
aagagactac cgtgttcgtg cagtgaaatt cagtacacta tgatcattcc tgtttccact      60

<210> SEQ ID NO 27
<211> LENGTH: 58
<212> TYPE: DNA
<213> ORGANISM: Artificial Sequence
<220> FEATURE:
<223> OTHER INFORMATION: Aptamer

<400> SEQUENCE: 27
```
acgtcaatgt taaactggtt caattacgcc ctgatactct tgactacgac tccgtact          58

<210> SEQ ID NO 28
<211> LENGTH: 60
<212> TYPE: DNA
<213> ORGANISM: Artificial Sequence
<220> FEATURE:
<223> OTHER INFORMATION: Aptamer

<400> SEQUENCE: 28
ccagcggcgg aggatacaaa aagtggatag gtttccgggg aatgcaatgt ttatggttgg          60

<210> SEQ ID NO 29
<211> LENGTH: 60
<212> TYPE: DNA
<213> ORGANISM: Artificial Sequence
<220> FEATURE:
<223> OTHER INFORMATION: Aptamer

<400> SEQUENCE: 29
atacgaaggt gtagttagcc gttcttagag tacagacgta ataaagcatg tgtccctcaa          60

<210> SEQ ID NO 30
<211> LENGTH: 59
<212> TYPE: DNA
<213> ORGANISM: Artificial Sequence
<220> FEATURE:
<223> OTHER INFORMATION: Aptamer

<400> SEQUENCE: 30
gatccacaga ctcagcttag tccgcttcgt gatctatcgc cgcccatacc cctatagta          59

<210> SEQ ID NO 31
<211> LENGTH: 59
<212> TYPE: DNA
<213> ORGANISM: Artificial Sequence
<220> FEATURE:
<223> OTHER INFORMATION: Aptamer

<400> SEQUENCE: 31
gcagatgtgg gacgactcaa cgatacacgg ggcacatgtc ctgcccgcga tgtcagccg          59

<210> SEQ ID NO 32
<211> LENGTH: 46
<212> TYPE: DNA
<213> ORGANISM: Artificial Sequence
<220> FEATURE:
<223> OTHER INFORMATION: Aptamer

<400> SEQUENCE: 32
tacattccca gtttcagaag tccctacttc ataccgacga tgctga                        46

<210> SEQ ID NO 33
<211> LENGTH: 8
<212> TYPE: DNA
<213> ORGANISM: Artificial Sequence
<220> FEATURE:
<223> OTHER INFORMATION: Aptamer

<400> SEQUENCE: 33 ggaatgta                                                                  8

<210> SEQ ID NO 34
<211> LENGTH: 38
<212> TYPE: DNA

```
<213> ORGANISM: Artificial Sequence
<220> FEATURE:
<223> OTHER INFORMATION: Aptamer

<400> SEQUENCE: 34
attcccagtt tcagaagtcc ctacttcata ccgacgat                              38

<210> SEQ ID NO 35
<211> LENGTH: 9
<212> TYPE: DNA
<213> ORGANISM: Artificial Sequence
<220> FEATURE:
<223> OTHER INFORMATION: Aptamer

<400> SEQUENCE: 35 tgaagtagg                                                              9

<210> SEQ ID NO 36
<211> LENGTH: 9
<212> TYPE: DNA
<213> ORGANISM: Artificial Sequence
<220> FEATURE:
<223> OTHER INFORMATION: Aptamer

<400> SEQUENCE: 36 tcgtcggta                                                              9

<210> SEQ ID NO 37
<211> LENGTH: 24
<212> TYPE: DNA
<213> ORGANISM: Artificial Sequence
<220> FEATURE:
<223> OTHER INFORMATION: Aptamer

<400> SEQUENCE: 37
gtttcagaag tccctacttc aaac                                             24

<210> SEQ ID NO 38
<211> LENGTH: 8
<212> TYPE: DNA
<213> ORGANISM: Artificial Sequence
<220> FEATURE:
<223> OTHER INFORMATION: Aptamer

<400> SEQUENCE: 38 tctgaaac                                                               8

<210> SEQ ID NO 39
<211> LENGTH: 8
<212> TYPE: DNA
<213> ORGANISM: Artificial Sequence
<220> FEATURE:
<223> OTHER INFORMATION: Aptamer

<400> SEQUENCE: 39 tagggact                                                               8
```